(12) United States Patent
Grass et al.

(10) Patent No.: US 7,435,848 B2
(45) Date of Patent: Oct. 14, 2008

(54) METHOD FOR PREPARING ALICYCLIC CARBOXYLIC ACIDS AND THEIR ESTERS

(75) Inventors: Michael Grass, Haltern am See (DE); Burkhard Reeken, Dorsten (DE); Axel Tuchlenski, Weinheim (DE); Alfred Kaizik, Marl (DE); Wilfried Büschken, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 310 days.

(21) Appl. No.: 11/322,349

(22) Filed: Jan. 3, 2006

(65) Prior Publication Data

US 2006/0167151 A1 Jul. 27, 2006

(30) Foreign Application Priority Data

Dec. 31, 2004 (DE) .................. 10 2004 063 637

(51) Int. Cl.
*C07C 61/12* (2006.01)
*C07C 61/00* (2006.01)
*C07C 69/74* (2006.01)

(52) U.S. Cl. .................. 562/498; 562/509; 560/116

(58) Field of Classification Search .............. None
See application file for complete search history.

(56) References Cited

U.S. PATENT DOCUMENTS

| 2004/0260113 A1 | 12/2004 | Bueschken et al. |
| 2005/0038285 A1 | 2/2005 | Maschmeyer et al. |
| 2005/0101800 A1 | 5/2005 | Bueschken et al. |
| 2006/0041167 A1 | 2/2006 | Grass et al. |
| 2006/0167151 A1 | 7/2006 | Grass et al. |
| 2006/0183936 A1 | 8/2006 | Grass et al. |
| 2007/0060768 A1 | 3/2007 | Grass et al. |

OTHER PUBLICATIONS

U.S. Appl. No. 11/739,345, filed Apr. 24, 2007, Grass et al.
U.S. Appl. No. 11/622,567, filed Jan. 12, 2007, Grass et al.
U.S. Appl. No. 11/911,691, filed Oct. 16, 2007, Grass et al.

*Primary Examiner*—Karl J Puttlitz
(74) *Attorney, Agent, or Firm*—Oblon, Spivak, McClelland, Maier & Neustadt, P.C.

(57) ABSTRACT

A method for the continuous preparation of an alicyclic carboxylic acid or an ester of the alicyclic carboxylic acid. A plastic which incorporates the alicyclic carboxylic acid or an ester of the alicyclic carboxylic acid. An article made of a plastic which incorporates the alicyclic carboxylic acid or an ester of the alicyclic carboxylic acid. A liquid which incorporates the alicycic carboxylic acid or an ester of the alicyclic carboxylic acid.

16 Claims, 1 Drawing Sheet

_US 7,435,848 B2_

METHOD FOR PREPARING ALICYCLIC CARBOXYLIC ACIDS AND THEIR ESTERS

CROSS REFERENCES TO RELATED APPLICATIONS

This application claims priority to German Patent No. 102004063637.0, filed on Dec. 31, 2004, which is incorporated herein by reference in its entirety.

BACKGROUND OF THE INVENTION

1. Field of the Invention

The present invention relates to a method for preparing alicyclic carboxylic acid(s) and their ester(s) by selective hydrogenation of the corresponding aromatic carboxylic acid(s), ester(s), and anhydride(s) in at least three series-connected reactors, at least the two first being operated in the loop operating mode.

2. Discussion of the Background

Alicyclic polycarboxylic esters, for example the esters of cyclohexane-1,2-dicarboxylic acid, are used as lubricating oil components and as aids in metal processing. In addition, they are used as plasticizers for polyolefins and PVC.

For plasticizing PVC, predominantly use is made of esters of phthalic acid, for example dibutyl, dioctyl, dinonyl or didecyl esters of phthalic acid. Since the use of these phthalates is increasingly controversial, their use in plastics could be restricted. Alicyclic polycarboxylic esters, of which some are already described in the literature as plasticizers for plastics, could be suitable substitutes.

In most cases, the most economical route for preparing alicyclic polycarboxylic esters is nuclear hydrogenation of the corresponding aromatic polycarboxylic esters, for example of the abovementioned phthalates. Some methods are already known for this:

In U.S. Pat. No. 5,286,898 and U.S. Pat. No. 5,319,129, methods are described by which dimethyl terephthalate can be hydrogenated in the presence of supported Pd catalysts doped with Ni, Pt and/or Ru at temperatures greater than or equal to 140° C. and at a pressure between 50 and 170 bar to give the corresponding hexahydrodimethyl terephthalate.

U.S. Pat. No. 3,027,398 discloses the hydrogenation of dimethyl terephthalate in the presence of supported Ru catalysts at 110 to 140° C. and 35 to 105 bar.

In DE 28 23 165, aromatic carboxylic esters are hydrogenated to the corresponding alicyclic carboxylic esters in the presence of supported Ni, Ru, Rh and/or Pd catalysts at 70 to 250° C. and 30 to 200 bar. In this case, use is made of a macroporous support having a mean pore size of 70 nm and a BET surface area of approximately 30 m²/g.

Supported ruthenium catalysts used for preparing alicyclic polycarboxylic esters by hydrogenating aromatic polycarboxylic esters are claimed in the patent documents WO 99/32427, WO 00/78704, DE 102 25 565.2 and DE 102 32 868.4.

WO 2004/046078 describes the hydrogenation of benzene-polycarboxylic acids or their derivatives in the presence of a catalyst which has the active catalyst metal applied on a support, the support having one or more materials with ordered mesopores.

In U.S. Pat. No. 3,027,398 aromatic polycarboxylic esters are hydrogenated batchwise. In U.S. Pat. No. 5,286,898, U.S. Pat. No. 5,319,129, DE 28 23 165, WO 99/32427 and WO 00/78704 aromatic polycarboxylic esters are hydrogenated continuously in a tubular reactor with or without recirculation (loop operating mode) of the hydrogenation output.

In DE 102 32 868.4 and DE 102 25 565.2, aromatic polycarboxylic esters are hydrogenated to the corresponding alicyclic polycarboxylic esters in two series-connected reactors, the first being operated in loop operating mode (partial recirculation of the reactor output) and the second being operated in straight through-flow passage. The first loop reactor can also be replaced by a plurality of small series- or parallel-connected loop reactors, these reactors having a shared circuit.

The technically known methods are not completely satisfactory with respect to the space-time yield and/or the selectivity.

SUMMARY OF THE INVENTION

Accordingly, it is one object of the present invention to provide a novel hydrogenation method for the continuous preparation of alicyclic carboxylic acid(s) and their ester(s) by catalytic hydrogenation of the corresponding aromatic acid(s), ester(s), and anhydride(s) such that the prepared alicyclic carboxylic acid(s) and their ester(s) can be used with only a small amount of purification.

It is another object of the present invention to provide a novel hydrogenation method for the continuous preparation of alicyclic carboxylic acid(s) and their ester(s) by catalytic hydrogenation of the corresponding aromatic acid(s), ester(s), and anhydride(s) such that the prepared alicyclic carboxylic acid(s) and their ester(s) can be used without purification.

It is a third object of the present invention provide a method for the continuous preparation of alicyclic carboxylic acid(s) and their ester(s) by catalytic hydrogenation of the corresponding aromatic acid(s), ester(s), and anhydride(s) that results in a more stable and flexible operating system.

A forth object of the present invention is to provide a method for the continuous preparation of alicyclic carboxylic acid(s) and their ester(s) by catalytic hydrogenation of the corresponding aromatic acid(s), ester(s), and anhydride(s) that simplifies maintenance of the reactor system and results in higher service life of the catalyst used.

A fifth object of the present invention is to provide mixtures of plastics comprising the inventively prepared alicyclic polycarboxylic acid(s) and their ester(s).

A sixth object of the present invention is to provide articles comprising mixtures of plastics comprising the inventively prepared alicyclic polycarboxylic acid(s) and their ester(s).

These and other objects, which will become apparent during the following detailed description, have been achieved by the inventor's discovery that in the hydrogenation of aromatic carboxylic acid(s), ester(s), and anhydride(s) to the corresponding alicyclic carboxylic acid(s) and their ester(s), the space-time yield and/or the product quality can be increased when the hydrogenation is carried out in at least three series-connected hydrogenation units, with at least the two first hydrogenation units being operated in loop operating mode.

BRIEF DESCRIPTION OF THE DRAWINGS

A more complete appreciation of the invention and many of the attendant advantages thereof will be readily obtained as the same become better understood by the reference to the following detailed description when considered in connection with the accompanying drawing, wherein.

Figure 1:
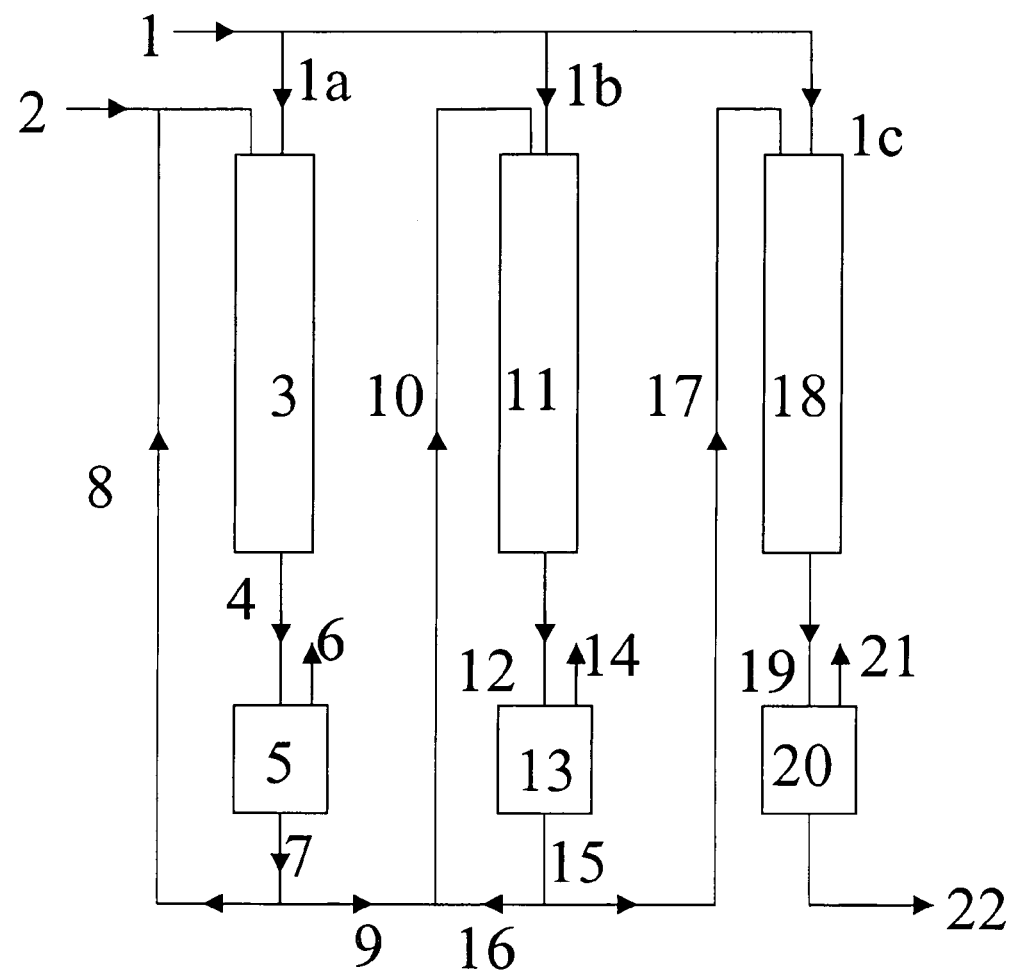
FIG. 1 is a diagram showing a variant of the present invention wherein three series-connected reactors, numbered 3, 11, and 18, are connected so that starting material enters at reactor number 2 and product exits from reactor number 18.

Reactors 3 and 11 are operated in loop operating mode and reactor 18 is operated in straight through-flow passage mode.

DETAILED DESCRIPTION OF THE PREFERRED EMBODIMENTS DEFINITIONS

As used herein the term "hydrogenation unit" is taken to mean a hydrogenation reactor or a plurality of series-connected reactors or a plurality of parallel-connected reactors or a reactor group which consists of parallel- and series-connected reactors, that is to say, a reactor or a reactor arrangement which can perform the function of a reactor in the inventive method.

In the context of the present invention, when residence times are mentioned, mean residence times (reciprocal LHSV) are meant. These are defined as the quotient of the given reaction volume or the bulk volume of the catalyst (in the case of heterogeneous reaction systems this is to be set as equal) and the total volumetric flow rate (without recycle stream) of the starting material (of the starting material to be hydrogenated).

The term "full ester" is intended to mean a compound in which all acid groups are esterified. "Partial esters" are compounds having at least one free acid group (or if appropriate one anhydride group) and at least one ester group.

The "circulation ratio" is the ratio of re-circulated hydrogenation output to starting material.

The present invention relates to a method for the continuous preparation of alicyclic carboxylic acid(s) and their ester(s) by catalytic hydrogenation of the corresponding aromatic carboxylic acid(s), ester(s), and anhydride(s) using a hydrogen-containing gas in the presence of solid catalysts disposed in the fixed bed, which comprises carrying out the hydrogenation in at least three series-connected hydrogenation units, operating at least the first two hydrogenation units in loop operating mode and operating at least two hydrogenation units which are series-connected and operated in loop operating mode with different residence times, the residence time in one of the hydrogenation units operated in loop operating mode being less than in a directly following hydrogenation unit operated in loop operating mode.

The inventive method has the advantage that, by a simple series connection of at least two loop reactors, the space-time yield can be increased compared with the methods described in the prior art. By the use of at least two loop reactors, in addition, a more stable and flexible operation is possible. For instance, in the event of loss of one of the loop reactors, the lost reactor can be bypassed, thus allowing the hydrogenation to continue. Owing to the use of the at least two loop reactors, therefore, higher breakdown security is also ensured. In addition, simpler maintenance of the reactor system and a higher service life of the catalysts is achieved.

The inventive method for the continuous preparation of alicyclic carboxylic acid(s) and their ester(s) by catalytic hydrogenation of the corresponding aromatic carboxylic acid(s), ester(s), and anhydride(s) by a hydrogen-containing gas in the presence of catalysts disposed in the fixed bed is distinguished by the fact that the hydrogenation is carried out in at least three series-connected hydrogenation units, that at least the first two hydrogenation units are operated in loop operating mode and that at least two hydrogenation units which are series-connected and operated in loop operating mode are operated with different residence times, the residence time in one of the hydrogenation units operated in loop operating mode being less than in a directly following hydrogenation unit operated in loop operating mode. It can be advantageous if all hydrogenation units are operated in loop operating mode. Likewise, it can be advantageous if the last hydrogenation unit is operated in straight through-flow passage.

The ratio of the residence times in the series-connected loop reactors is preferably from 0.01 to less than 1, preferably from 0.1 to 0.9, and particularly preferably from 0.2 to 0.5. The residence times are preferably set in such a manner that, in the first of the series-connected loop reactors, a conversion rate of 40 to 90% is achieved, preferably from 60 to 90%, and in the second loop reactor, a conversion rate of 2 to 60%, preferably of 2 to 40%, based on the starting concentration of the compound to be hydrogenated at the input of the respective reactor.

Owing to the use of two series-connected loop reactors with differing residence times and an operating mode in the range of the particularly preferred conversion rates, in the hydrogenation of diisononyl phthalates or didecyl phthalates (diisodecyl phthalates), optimum utilization of the catalyst volume is achieved.

Of course, more than two series-connected loop reactors can be present in the inventive method. It is also possible in the inventive method that when more than two series-connected loop reactors are present, the series-connected loop reactors are not run with different residence times. For example, a front reactor could be operated with a lower residence time than the following two series-connected reactors.

In the inventive method, an aromatic carboxylic acid or an ester thereof or an anhydride thereof or a mixture of one or more aromatic carboxylic acids and/or one or more esters of the corresponding aromatic carboxylic acids and/or one or more anhydrides of the corresponding aromatic carboxylic acids can be continuously hydrogenated. The hydrogenation occurs in the liquid phase or in a liquid/gas mixed phase in the presence of a catalyst disposed in the fixed beds of at least three series-connected hydrogenation units. In this arrangement, hydrogen is added to the aromatic carboxylic acid or ester thereof or anhydride thereof or mixture form the corresponding alicyclic carboxylic acid(s) and/or carboxylic acid ester(s). A variant of the inventive method with three hydrogenation units is shown as block diagram in FIG. 1. It must be emphasized that the variant shown here also applies mutatis mutandis to methods having more than three hydrogenation units.

In the embodiment of the invention shown in FIG. 1, the first two hydrogenation units (numbers 3 and 11) are operated in loop operating mode and the third hydrogenation unit (number 18) is operated in straight through-flow passage mode. Other embodiments are possible in which all three hydrogenation units are operated in loop operating mode, or in which more than three hydrogenation units are present. If the hydrogenation is carried out in a hydrogenation plant having more than three hydrogenation units, according to the invention, the first two hydrogenation units are operated in loop operating mode and the following hydrogenation units can optionally be operated in loop operating mode or in straight through-flow passage mode.

In the variant of the inventive method shown in FIG. 1, each individual reactor is charged with hydrogenation gas. In order to minimize hydrogen consumption and the output losses caused by the offgas streams, it can be expedient to use the offgas of one hydrogenation unit as hydrogenation gas for another hydrogenation unit. For example, in a method as shown in FIG. 1, the offgas (6) from the first hydrogenation unit (3) can be fed into the second hydrogenation unit (11) instead of the hydrogenation gas (1b), and the offgas (14) of the second hydrogenation unit (11) can be fed into the third hydrogenation unit (18) instead of the hydrogenation gas (1c). In this case, liquid starting material/product phase and hydrogenation gas flow in the same sequence through the reactors. Likewise, it can be expedient to allow hydrogenation gas and starting material/product phase to flow through the reactors in opposite directions. In this case, fresh hydrogenation gas is introduced into the last reactor and offgas from the first reactor is discharged. Furthermore, two or more reactors can have a shared hydrogenation gas system and other reactors can be charged separately therefrom with hydrogenation gas. When the offgas of one reactor is used as hydrogenation gas of another reactor, if desired, the pressure drop can be compensated for by intermediate compression.

Preferably, the offgas quantities and gas streams are set in such a manner that all reactors possess good fluid dynamics, i.e. a low wall flows and a high interfacial areas for mass transfer.

As hydrogenation gases, use can be made of any desired hydrogen-containing gas mixtures which do not comprise harmful amounts of catalyst poisons such as carbon monoxide or hydrogen sulfide. The use of inert gases is optional. Preferably, hydrogen at a purity greater than 95%, in particular greater than 98%, is used. Inert gas fractions can be, for example, nitrogen or methane. Preferably, sufficient hydrogen is present in the hydrogenation units so that it is present in excess, in particular in an excess of 200%, preferably in an excess of from 5 to 100%, and particularly preferably in an excess of from 10 to 50%, based on the stoichiometric amount which is required to achieve the conversion rate which is possible or desired in the hydrogenation unit. Without setting a sufficient excess of hydrogen, the hydrogenation of the aromatic bonds is achieved only incompletely, which leads to losses of yield. According to the inventive method, aromatic carboxylic acid(s) and/or their ester(s) and/or their anhydride(s), such as aromatic mono-, di- or polycarboxylic acid(s) and/or aromatic mono-, di- or polycarboxylic ester(s) and/or aromatic mono-, di- or polycarboxylic anhydride(s), in particular their alkyl ester(s), can be reacted to give the corresponding alicyclic carboxylic acid(s) and/or alicyclic carboxylic ester(s) compounds. As aromatic di- or polycarboxylic acid esters, not only full esters, but also partial esters can be hydrogenated using the inventive method. If polycarboxylic esters are used in the inventive method, these preferably comprise 2, 3 or 4 ester functions.

In the inventive method, as aromatic di- or polycarboxylic acids and their esters, use is preferably made of benzene-, diphenyl-, naphthalene-, diphenyl oxide- or anthracene-polycarboxylic acids, their anhydrides and/or the corresponding esters. The alicyclic di- or polycarboxylic acids or their esters obtained by the inventive method consist of one or more $C_6$ rings, if appropriate linked by a C—C bond, or fused.

In a preferred embodiment, the present invention relates to a method for hydrogenating 1,2-, 1,3- or 1,4-benzenedicarboxylic acid or esters thereof, and/or 1,2,3-, 1,2,4- or 1,3,5-benzenetricarboxylic acid or esters thereof, i.e. the isomers of 1,2-, 1,3- or 1,4-cyclohexanedicarboxylic acid or esters thereof, or 1,2,3-, 1,3,5- or 1,2,4-cyclohexanetricarboxylic acid or esters thereof are obtained.

In the inventive method, for example, the following aromatic carboxylic acids or esters, can be used: 1,2-naphthalenedicarboxylic acid, 1,3-naphthalenedicarboxylic acid, 1,4-naphthalenedicarboxylic acid, 1,5-naphthalenedicarboxylic acid, 1,6-naphthalenedicarboxylic acid, 1,7-naphthalenedicarboxylic acid, 1,8-naphthalenedicarboxylic acid, phthalic acid (benzene-1,2-dicarboxylic acid), isophthalic acid (benzene-1,3-dicarboxylic acid), terephthalic acid (benzene-1,4-dicarboxylic acid), benzene-1,2,3-tricarboxylic acid, benzene-1,2,4-tricarboxylic acid (trimellitic acid), benzene-1,3,5-tricarboxylic acid (trimesic acid), benzene-1,2,3,4-tetracarboxylic acid. Use can be made of acids or their esters, which are formed from said acids by substitution by alkyl, cycloalkyl or alkoxyalkyl groups of one or more hydrogen atoms bound to the aromatic nucleus.

As aromatic monocarboxylic acids or their esters, use can be made in the inventive method of benzoic acid, 1-naphthoic acid or 2-naphthoic acid or their esters. Furthermore, use can be made of monocarboxylic acids or their esters, which are formed from said monocarboxylic acids by substitution by alkyl, cycloalkyl or alkoxyalkyl groups of one or more hydrogen atoms bound to the aromatic nucleus.

Particularly preferably, use can be made in the inventive method of the aromatic carboxylic esters of the above-mentioned aromatic carboxylic acids. The alcohol component of the aromatic carboxylic esters preferably used preferably consists of branched or linear (unbranched) alkyl, cycloalkyl or alkoxyalkyl groups having 1 to 25 carbon atoms, preferably 3 to 15, particularly preferably 8 to 13, carbon atoms, and very particularly preferably 9 or 10 carbon atoms. The alcohol component can have one or more hydroxyl groups. If more than one carboxyl group is present in a molecule, the alcohol components in a molecule of an aromatic polycarboxylic ester used can be identical or different, i.e. they can have identical or different isomers or chain lengths. Obviously, isomers with respect to the substitution pattern of the aromatic system can also be used in the form of a mixture, e.g. a mixture of phthalic ester and terephthalic ester.

In the inventive method, as an ester of an aromatic di- or polycarboxylic acid, use can be made of, for example, the following compounds: terephthalic acid monomethyl ester, terephthalic acid dimethyl ester, terephthalic acid diethyl ester, terephthalic acid di-n-propyl ester, terephthalic acid dibutyl ester, terephthalic acid diisobutyl ester, terephthalic acid di-tert-butyl ester, terephthalic acid monoglycol ester, terephthalic acid diglycol ester, terephthalic acid diisoheptyl ester, terephthalic acid n-octyl ester, terephthalic acid diisooctyl ester, terephthalic acid di-2-ethylhexyl ester, terephthalic acid di-n-nonyl ester, terephthalic acid diisononyl ester, terephthalic acid di-n-decyl ester, terephthalic acid diisodecyl ester, terephthalic acid dipropylheptyl ester, terephthalic acid di-n-undecyl ester, terephthalic acid diisododecyl ester, terephthalic acid ditridecyl ester, terephthalic acid di-n-octadecyl ester, terephthalic acid diisooctadecyl ester, terephthalic acid di-n-eicosyl ester, terephthalic acid monocyclohexyl ester; phthalic acid monomethyl ester, phthalic acid dimethyl ester, phthalic acid di-n-propyl ester, phthalic acid di-n-butyl ester, phthalic acid diisobutyl ester, phthalic acid di-tert-butyl ester, phthalic acid monoglycol ester, phthalic acid diglycol ester, phthalic acid diisoheptyl ester, phthalic acid di-n-octyl ester, phthalic acid diisooctyl ester, phthalic acid diethylhexyl ester, phthalic acid di-n-nonyl ester, phthalic acid diisononyl ester, phthalic acid di-n-decyl ester, phthalic acid di-2-propylheptyl ester, phthalic acid diisodecyl ester, phthalic acid di-n-undecyl ester, phthalic acid diisoundecyl ester, phthalic acid ditridecyl ester, phthalic acid di-n-octadecyl ester, phthalic acid diisooctadecyl ester, phthalic acid di-n-eicosyl ester, phthalic acid monocyclohexyl ester; phthalic acid dicyclohexyl ester, isophthalic acid monomethyl ester, isophthalic acid dimethyl ester, isophthalic acid dimethyl ester, isophthalic acid diethyl ester, isophthalic acid di-n-propyl ester, isophthalic acid di-n-butyl ester, isophthalic acid diisobutyl ester, isophthalic acid di-tert-butyl ester, isophthalic acid monoglycol ester, isophthalic acid diglycol ester, isophthalic acid diisoheptyl ester, isophthalic acid di-n-octyl ester, isophthalic acid diisooctyl ester, isophthalic acid di-2-ethylhexyl ester, isophthalic acid di-n-nonyl ester, isophthalic acid diisononyl ester, isophthalic acid di-n-decyl ester, isophthalic acid diisodecyl ester, isophthalic acid dipropylheptyl ester, isophthalic acid di-n-undecyl ester, isophthalic acid diisododecyl ester, isophthalic acid di-n-dodecyl ester, isophthalic acid ditridecyl ester, isophthalic acid di-n-octadecyl ester, isophthalic acid diisooctadecyl ester, isophthalic acid di-n-eicosyl ester, isophthalic acid monocyclohexyl ester.

In the inventive method, as an ester of the monocarboxylic acids, use can be made of, for example, benzoates of diols, for example glycol dibenzoate, diethylene glycol dibenzoate, triethylene glycol dibenzoate or dipropylene glycol dibenzoate, or else benzoic acid alkyl ester, for example decyl or isodecyl benzoate, nonyl or isononyl benzoate, octyl or isooctyl benzoate, 2-ethylhexyl benzoate or tridecyl or isotridecyl benzoate.

In the inventive method, use can also be made of mixtures of two or more carboxylic acids or carboxylic acid esters, in particular mixtures of carboxylic esters. Such mixtures can be obtained, for example, in the following ways:

a) a di- or polycarboxylic acid is partially esterified with an alcohol in such a manner that full and partial esters are present simultaneously.
b) a mixture of at least two carboxylic acids is esterified with an alcohol, a mixture of at least two full esters being formed.
c) a di- or polycarboxylic acid is esterified with an alcohol mixture, in which case a corresponding mixture of full esters can be formed.
d) a di- or polycarboxylic acid is partially esterified with an alcohol mixture.
e) a mixture of at least two carboxylic acids is partially esterified with an alcohol mixture.
f) a mixture of at least two di- or polycarboxylic acids is partially esterified with an alcohol mixture.

In these reactions, instead of the polycarboxylic acids, the corresponding anhydrides can also be used.

On a large scale, aromatic esters, in particular the full esters, are prepared by method c), frequently from alcohol mixtures. Corresponding alcohol mixtures are, for example:

$C_5$-alcohol mixtures, prepared from linear butenes by hydroformylation and subsequent hydrogenation;

$C_5$-alcohol mixtures, prepared from isobutene or butene mixtures which comprise linear butenes and isobutene, by hydroformylation and subsequent hydrogenation;

$C_6$-alcohol mixtures, prepared from a pentene or a mixture of two or more pentenes, by hydroformylation and subsequent hydrogenation;

$C_7$-alcohol mixtures, prepared from triethylene or dipropene or a hexene isomer or another mixture of hexene isomers by hydroformylation and subsequent hydrogenation;

$C_8$-alcohol mixtures, such as 2-ethylhexanol (2 isomers), prepared by aldol condensation of n-butyraldehyde and subsequent hydrogenation;

$C_9$-alcohol mixtures, prepared from $C_4$-olefins by dimerization, hydroformylation and hydrogenation. For preparation of the $C_9$-alcohols, starting materials which can be used are isobutene or a mixture of linear butenes or mixtures with linear butenes and isobutene. The $C_4$-olefins can be dimerized using different catalysts, for example proton acids, zeolites, organometallic nickel compounds or solid nickel-containing contact catalysts. The $C_8$-olefin mixtures can be hydroformylated using rhodium or cobalt catalysts. There is therefore a multiplicity of technical $C_9$-alcohol mixtures.

$C_{10}$-alcohol mixtures prepared from tripropylene by hydroformylation and subsequent hydrogenation; 2-propylheptanol (2 isomers), prepared by aldol condensation of valeraldehyde and subsequent hydrogenation;

$C_{10}$-alcohol mixtures, prepared from a mixture of at least two $C_5$-aldehydes by aldol condensation and subsequent hydrogenation; and $C_{13}$-alcohol mixtures, prepared from dihexene, hexaethylene, tetrapropylene or tributene by hydroformylation and subsequent hydrogenation.

Further alcohol mixtures can be produced by hydroformylation and subsequent hydrogenation from olefins or olefin mixtures which arise, for example, in Fischer-Tropsch syntheses, in dehydrogenations of hydrocarbons, in metathesis reactions, in the polygas method or in other industrial processes. Furthermore, olefin mixtures comprising olefins of different carbon numbers can also be used for preparing alcohol mixtures.

In the inventive method, use can be made of all ester mixtures prepared from aromatic carboxylic acids and the above-mentioned alcohol mixtures. According to the invention, use is preferably made of esters prepared from phthalic acid, phthalic anhydride or benzoic acid and a mixture of isomeric alcohols having from 6 to 13 carbon atoms.

Examples of technical phthalates which can be used in the inventive method are the following products having the trade names:

Vestinol C (di-n-butyl phthalate) (CAS No. 84-74-2); Vestinol IB (diisobutyl phthalate) (CAS No. 84-69-5); Jayflex DINP (CAS No. 68515-48-0); Jayflex DIDP (CAS No. 68515-49-1); Palatinol 9P (68515-45-7), Vestinol 9 (CAS No. 28553-12-0); TOTM (CAS No. 3319-31-1); Linplast 68-TM, Palatinol N (CAS No. 28553-12-0); Jayflex DHP (CAS No. 68515-50-4); Jayflex DIOP (CAS No. 27554-26-3); Jayflex UDP (CAS No. 68515-47-9); Jayflex DIUP (CAS No. 85507-79-5); Jayflex DTDP (CAS No. 68515-47-9); Jayflex L9P (CAS No. 68515-45-7); Jayflex L911P (CAS No. 68515-43-5); Jayflex L11P (CAS No. 3648-20-2); Witamol 110 (CAS No. 68515-51-5); Witamol 118 (di-n-$C_8$-$C_{10}$-alkyl phthalate) (CAS No. 71662-46-9); Unimoll BB (CAS No. 85-68-7); Linplast 1012 BP (CAS No. 90193-92-3); Linplast 13XP (CAS No. 27253-26-5); Linplast 610P (CAS No. 68515-51-5); Linplast 68 FP (CAS No. 68648-93-1); Linplast 812 HP (CAS No. 70693-30-0); Palatinol AH (CAS No. 117-81-7); Palatinol 711 (CAS No. 68515-42-4); Palatinol 911 (CAS No. 68515-43-5); Palatinol 11 (CAS No. 3648-20-2); Palatinol Z (CAS No. 26761-40-0); Palatinol DIPP (CAS No. 84777-06-0); Jayflex 77 (CAS No. 71888-89-6); Palatinol 10 P (CAS No. 533-54-0); Vestinol AH (CAS No. 117-81-7).

It must be noted that in the nuclear hydrogenation of aromatic di- or polycarboxylic acid(s) or their ester(s) from each isomer used, at least two stereoisomeric hydrogenation products can form. The mass ratios of the resultant stereoisomers depend on the catalyst used and on the hydrogenation conditions. All hydrogenation products having ratio(s) of stereoisomers can be used either without separation, or after a separation. Generally, the hydrogenation products are used without separation.

In the inventive method, solid hydrogenation catalysts are used which preferably comprise at least one metal of the eighth subgroup of the Periodic Table of the Elements. Preferably, use is made, as active metals of the eighth subgroup of the Periodic Table of the Elements, of platinum, rhodium, palladium, cobalt, nickel, ruthenium, or a mixture of two or more thereof, in particular ruthenium being used as active metal.

In addition to the abovementioned metals, at least one metal of the first and/or seventh subgroup of the Periodic Table of the Elements may be present in the catalysts. Preferably, use is made of rhenium and/or copper.

The content of the active metals, i.e. of the metals of the first and/or seventh and/or eighth subgroup of the Periodic Table of the Elements, is preferably from 0.1 to 30% by mass. The noble metal content, i.e. of the metals of the eighth subgroup of the Periodic Table of the Elements and of the fifth or sixth period, e.g. palladium, ruthenium, calculated as metal, is preferably in the range from 0.1 to 10% by mass, in particular in the range from 0.8 to 5% by mass, very particularly between 1 and 3% by mass.

Preferably, the catalysts used are supported catalysts. As supports, use can be made, for example, of the following materials: activated carbon, silicon carbide, aluminum oxide, silicon oxide, aluminosilicate, titanium dioxide, zirconium dioxide, magnesium oxide and/or zinc oxide or their mixtures. Particularly preferably, use is made of a catalyst which has a titanium dioxide support. In addition, these support materials can comprise alkali metals, alkaline earth metals and/or sulfur.

In the inventive method, preferably use is made of ruthenium catalysts which are claimed in the patent documents DE 102 25 565.2 and DE 102 32 868.4, the contents of which are herein incorporated by reference.

In the inventive method, the hydrogenation units preferably each consist of a hydrogenation reactor. This can be a tubular reactor, tube-bundle reactor, or preferably a shaft reactor.

The individual reactors can be operated adiabatically, polytropically or virtually isothermally, i.e. having a temperature increase of typically less than 10° C. In this case, in particular the reactors operated in the loop operating mode are preferably run quasiisothermally, preferably having a temperature increase less than 10° C., particularly preferably less than 5° C.

The inventive method is carried out preferably in the liquid/gas mixed phase or liquid phase, in three-phase reactors in cocurrent flow, the hydrogenation gas being distributed in a manner known in the liquid starting material/product stream. In the interest of even liquid distribution, and improved removal of heat of reaction and/or a high space-time yield, the reactors operated in the loop operating mode are preferably run at high liquid loadings of from 10 to 400, preferably from 20 to 200, and particularly preferably from 40 to 150 m$^3$ per m$^2$ cross-sectional area of the empty reactor hour.

The liquid loadings can be identical or different in the reactors operated in the loop operating mode. Preferably, the liquid loading is greatest in the first reactor and decreases in the subsequent reactors operated. In a plant, according to the invention having two series-connected loop reactors, the liquid loading in the first reactor is preferably in the range from 20 to 200, in particular in the range from 40 to 150 m$^3$/(m$^2$·h) and in the second reactor, preferably in the range from 20 to 180, in particular in the range from 40 to 140 m$^3$/(m$^2$·h).

The loading of the reactor operated in the straight through-flow passage mode is preferably from 2 to 100 m$^3$/(m$^2$·h), in particular from 10 to 80 m$^3$/(m$^2$·h).

The hydrogenation can be carried out in the absence, or preferably in the presence, of a solvent. As solvent, use can be made of all liquids which form a homogeneous solution with the starting material and product, which are inert under hydrogenation conditions and which may readily be separated off from the product. The solvent can also be present in a mixture of a plurality of substances, and, if appropriate, water.

Use can be made, for example, of the following substances as solvent(s): straight-chain or cyclic ethers, for example tetrahydrofuran or dioxane, and also aliphatic alcohols in which the alkyl radical has 1 to 13 carbon atoms. Alcohols which can preferably be used as solvents are isopropanol, n-butanol, isobutanol, n-pentanol, 2-ethylhexanol, nonanols, technical nonanol mixtures, decanol, technical decanol mixtures, and tridecanols. The use of alcohols is only preferred when the carboxylic acid esters are hydrogenated are. When alcohols are used as solvent(s), it can be expedient to use the alcohol or alcohol mixture which would be formed on saponification of the product. As a result, byproduct formation due to transesterification would be excluded. A further preferred solvent is the hydrogenation product itself.

By using a solvent, the aromatics concentration in the reactor feed can be limited, as a result of which better temperature control in the reactor can be achieved. This can have as a consequence minimization of side reactions which, in turn, leads to an increase in product yield. Preferably, the aromatics content in the reactor feed is between 1 and 70%. The desired concentration range can, in those reactors which are operated in the loop operating mode, be set by the circulation ratio (ratio of recirculated hydrogenation output to starting material). The aromatics concentration in the reactor feed (mixture of fresh starting material or hydrogenation output of the previous reactor and of circulation stream) preferably decrease from the first to the last reactor. For example, in a plant according to FIG. 1, the aromatics concentration in the feed to the first reactor (3) is in the range from 70 to 5% by mass, in the feed to the second reactor (11) in the range from 40 to 2% by mass, and in the feed to the third reactor (18) in the range from 20 to 1% by mass.

The inventive method is carried out preferably in a pressure range from 0.3 to 30 MPa, in particular from 1.5 to 20 MPa, very particularly preferably from 5 to 20 MPa. The pressure in the individual reactors can be identical or different. Preferably, the pressures are identical or approximately identical.

The hydrogenation temperatures range preferably from 50 to 250° C., more preferably from 80 to 200° C. The hydrogenation temperatures in individual reactors can be identical or different.

The hydrogenation product which is formed in the inventive hydrogenation of an aromatic carboxylic acid or its ester, in particular an aromatic di- or polycarboxylic ester or a mixture of aromatic di- or polycarboxylic esters by the inventive method has preferably a content of alicyclic carboxylic acids or their esters, of greater than 96% by mass, in particular greater than 98% by mass, very particularly preferably greater than 99% by mass. This mixture can be used directly or after a purification. Byproducts can be separated off, for example, by distillation, or by stripping with an inert gas such as nitrogen or steam. Preferably, small amounts of low boiling solvent(s) are separated off by stripping with steam in the temperature range from 120° C. to 240° C., in particular in the range from 150 to 200° C. and at a pressure of from 5 kPa to 10 kPa. Then, by reducing the pressure to below 5 kPa, the product can be dried.

Products which are obtained by the inventive method are mixtures which comprise alicyclic carboxylic acid(s) or their ester(s), in particular alicyclic carboxylic ester(s), and particularly preferably alicyclic di- or polycarboxylic acid(s).

The present invention further relates to the use of the inventively prepared mixtures of alicyclic carboxylic esters as plasticizers in plastics. Preferred plastics are PVC, homo- and copolymers based on ethylene, propylene, butadiene, vinyl acetate, glycidyl acrylate, glycidyl methacrylate, methacrylates, acrylates, acrylates having, bound to the oxygen atom of the ester group, alkyl radicals of branched or unbranched alcohols having one to ten carbon atom(s), styrene, acrylonitrile, homo- or copolymers of cyclic olefins.

As representatives of the above groups, the following plastics may be mentioned by way of example: polyacrylates having identical or different alkyl radicals having 4 to 8 carbon atoms, bound to the oxygen atom of the ester group, in particular having the n-butyl, n-hexyl, n-octyl and 2-ethylhexyl radical and isononyl radical, polymethacrylate, polymethylmethacrylate, methylacrylate-butylacrylate copolymers, methylmethacrylate-butylmethacrylate copolymers, ethylene-vinylacetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers and/or nitrocellulose.

Furthermore, the inventively prepared alicyclic carboxylic esters can be used for modifying plastic mixtures, in particular for blending a polyolefin with a polyamide. Mixtures of plastics and the inventively prepared alicyclic polycarboxylic esters are likewise subject matter of the present invention. Suitable plastics are the abovementioned compounds. Such mixtures preferably comprise at least 5% by mass, particularly preferably 10-80% by mass, very particularly preferably 20-70% by mass, of the alicyclic polycarboxylic esters.

Mixtures of plastics, in particular PVC, which comprise one or more of the inventively prepared alicyclic polycarboxylic esters can, for example, be present in the following products, or be used for their preparation: hoses, cables, wire sheathings, insulating tapes, in motor vehicle and furniture construction, plastisols, in floor coverings, medical articles, food packaging, seals, films, composite films, plates, artificial leather, toys, wallpaper, packaging vessels, adhesive tape films, clothing, coatings, coatings of textiles, shoes, underseal, seam seals, modeling compositions, or balls.

In addition to the abovementioned applications, the inventively prepared alicyclic carboxylic esters can be used as lubricating oil component, as constituent of cooling fluids and metal processing liquids. Likewise, they can be used as component in paints, varnishes, inks and adhesives.

The inventive method can be carried out in various embodiments. A preferred embodiment of the present invention is shown by way of example as a block diagram in the figure FIG. 1. This diagram has three reactors or reactor units of which two are operated in the loop operating mode. Of course, the inventive method can also be carried out using more than three reactors (or reactor units), or all three reactors can be operated in the loop operating mode.

In the variant of the inventive method according to FIG. 1, hydrogen (1a), starting material (2) and a part (8) of the liquid hydrogenation output (7) from the reactor (3) are fed into the hydrogenation unit (3). The hydrogenation output (4) from the hydrogenation unit (3) is separated in the still (5) into offgas (6) and liquid phase (7). A part (9) of the stream (7) is passed together with the part (16) of the liquid phase (15) from the second hydrogenation unit (11) and hydrogen (1b) into the hydrogenation unit (11). The hydrogenation output (12) from the hydrogenation unit (11) is separated in the still (13) into offgas (14) and liquid phase (15). A part (17) of the stream (15) is fed together with hydrogen (1c) into the hydrogenation unit (18). The hydrogenation output (19) from the hydrogenation unit (18) is separated in the still (20) into offgas (21) and crude product (22). Crude product (22) is either used as such or, after purification, in a plant which is not shown.

EXAMPLES

In the following examples, all temperatures are in degrees Celsius, all pressures are in megapascals, S.T.P stands for standard temperature and pressure, l stands for liter, h stands for hour, DINP stands for diisononyl phthalate, and DINCH stands for 1,2-cyclohexanedicarboxylic acid, diisononyl ester.

The present invention is described by way of example in the examples hereinafter. Obviously, numerous modifications and variations of the present invention are possible in light of the above teachings. It is therefore to be understood that, within the scope of the appended claims, the invention may be practiced otherwise than as specifically described herein.

All patents and other references mentioned below are incorporated in full herein by this reference, the same as if set forth at length.

The hydrogenation reactor was a tubular reactor and was operated continuously, optionally in straight through-flow passage mode, or in loop operating mode. In all experiments, the liquid phase and the hydrogenation gas flowed cocurrently from top to bottom.

The tubular reactor was packed with 1350 ml of ruthenium catalyst (1% Ru/TiO$_2$). This catalyst was prepared from the TiO$_2$ support Aerolyst 7711 and an aqueous ruthenium nitrate solution as described in DE 102 32 868.4. The catalyst consisted of cylindrical rod extrudates having the circle diameter of 1.5 mm and a length of 4 to 6 mm.

In both experiments, diisononyl phthalate, abbreviated form DINP, of Oxeno Olefinchemie GmbH having the trade name Vestinol 9 was used. As hydrogenation gas, use was made of hydrogen at a purity of greater than 99.9%.

In both examples the liquid hydrogenation output of one hydrogenation stage is the feed product of the next hydrogenation stage. The individual hydrogenation stages were carried out one after the other in the same reactor using the same catalyst and same catalyst quantity. The hydrogenation output of the first stage, after the quasisteady-state equilibrium is achieved, was collected and used for the second stage. In example 1, in addition, the hydrogenation output of the second stage was collected as feed material for the third stage. For better comparability, the pressure, the reaction temperature and the offgas amount were identical in all hydrogenation steps.

Example 1

Example 1 is according to the present invention. In this example DINP was converted to DINCH by hydrogenation. The hydrogenation was carried out in three stages. In the first two stages, the reactor was operated in loop operating mode, and in the third stage the reactor was operated in straight through-flow passage mode. The operating parameters and the mass flow rates of example 1 are compiled in Table 1.

TABLE 1

|  | 1st stage | 2nd stage | 3rd stage |
| --- | --- | --- | --- |
| Temperature (° C.) | 100 | 100 | 100 |
| Pressure (MPa) | 10 | 10 | 10 |
| Offgas (l(S.T.P.)/h) | 50 | 50 | 50 |
| Circulation rate (l/h) | 30 | 30 | 0 |

TABLE 1-continued

|  | 1st stage | 2nd stage | 3rd stage |
|---|---|---|---|
| Feed (l/h) | 9.54 | 3.18 | 1.05 |
| DINP concentration in the feed (%) (based on fresh DINP or hydrogenation output of the previous reactor) | 100 | 59.7 | 19.9 |
| Hydrogenation output (l/h)* | 9.592 | 3.197 | 1.053 |
| DINP concentration in the hydrogenation output (%) | 59.7 | 19.9 | <0.05 |
| LHSV ($h^{-1}$)** | 7.06 | 2.35 | 0.78 |

*Volume of the hydrogenation output, calculated assuming a density of 0.975 g/l and ignoring the offgas losses
**LHSV: liters of fresh DINP or liters of hydrogenation output from the previous reactor per liter of catalyst per hour The target product (hydrogenation output of the third stage) had a purity of greater than 99.5% by mass. The DINP conversion rate was virtually quantitative.

Taking into account the fact that the hydrogenation output of one stage is the feed material of the next stage, starting from 9.54 l/h of fresh DINP, for a continuous hydrogenation taking into account the differing densities of DINP and DINCH, gave the following feed streams (without recycle streams) to the reactors:

First reactor: 9.54 l/h

Second reactor: 9.592 l/h

Third reactor: 9.643 l/h

Maintaining the LHSV identified in Table 1 gave, for the just-mentioned volumetric flow rates, the following catalyst amounts:

First reactor: 1.35 l

Second reactor: 4.07 l

Third reactor: 12.36 l

The (total) catalyst volume in the two loop reactors corresponds accordingly to 5.432 l. The feed of 9.54 l/h of fresh DINP to the first reactor, over the two loop reactors, gave a total LHSV of 1.75 $h^{-1}$.

Example 2

Example 2 is a comparative example. In this example DINP was converted to DINCH by hydrogenation. The hydrogenation was carried out in two stages. In the first stage, the reactor was operated in loop operating mode, and in the second stage in straight through-flow passage.

The operating parameters and the mass flow rates of example 2 are listed in Table 2.

TABLE 2

|  | 1st stage | 2nd stage |
|---|---|---|
| Temperature (° C.) | 100 | 100 |
| Pressure (MPa) | 10 | 10 |
| Offgas (l(S.T.P.)/h) | 50 | 50 |
| Circulation rate (l/h) | 30 | 0 |
| Feed (l/h) | 1.59 | 1.05 |
| DINP concentration in the feed (%) (based on fresh DINP or hydrogenation output of the previous reactor) | 100 | 19.9 |
| Hydrogenation output (l/h) | 1.625 | 1.053 |
| DINP concentration in the hydrogenation output (%) | 19.9 | <0.05 |
| LHSV ($h^{-1}$) | 1.18 | 0.78 |

Example 1 is superior to Comparative Example 2 in terms of space-time yield. In Example 1, the hydrogenation of pure DINP to a residual content of 19.9% was performed in two series-connected loop reactors having an LHSV of 1.75 $h^{-1}$. Contrastingly, in Comparative Example 2, in the hydrogenation to the same residual content using only one loop reactor, the LHSV was 1.18 $h^{-1}$. It was thus found that the inventive method has a higher space-time yield compared with a conventional method.

The invention claimed is:

1. A method for the continuous preparation of an alicyclic carboxylic acid or an ester thereof comprising
   catalytically hydrogenating an aromatic carboxylic acid, an ester thereof, an anhydride thereof, or a mixture of two or more of these, with a hydrogen-comprising gas in the presence of at least one solid catalyst disposed in a fixed bed,
   wherein the hydrogenation is carried out in at least three series-connected hydrogenation units;
   wherein at least the first two series-connected hydrogenation units of the at least three series-connected hydrogenation units are operated in loop operating mode;
   wherein the at least the first two series-connected hydrogenation unites operating in loop operating mode operate with different residence times, and
   wherein the residence time in one of the at least first two series-connected hydrogenation units operating in loop operating mode is less than the residence time in a directly following hydrogenation unit operating in loop operating mode.

2. The method as claimed in claim 1, wherein all hydrogenation units are operated in loop operating mode.

3. The method of claim 1, wherein the last hydrogenation unit is operated in straight through-flow passage mode.

4. The method of claim 1, wherein the hydrogenation is carried out in an apparatus comprising three hydrogenation units.

5. The method of claim 1, wherein the at least one solid catalyst comprises at least one metal of the eighth subgroup of the Periodic Table of the Elements.

6. The method of claim 5, wherein the at least one solid catalyst comprises ruthenium.

7. The method of claim 1, wherein the at least one solid catalyst comprises a titanium dioxide support.

8. The method of claim 1, wherein the ratio of the residence times in the series-connected loop reactors is from 0.01 to less than 1.

9. The method of claim 1, wherein the aromatic carboxylic acid comprises an aromatic mono-, di- or poly-carboxylic acid.

10. The method of claim 9, wherein the aromatic mono-, di- or polycarboxylic acid comprises benzene-, diphenyl-, naphthalene-, diphenyl oxide- or anthracene di- or poly-carboxylic acid.

11. The method of claim 9, wherein the aromatic monocarboxylic acid comprises benzoic acid, 1-naphthoic acid, or 2-naphthoic acid.

12. The method as claimed in claim 11, wherein the ester of the monocarboxylic acid is isononyl benzoate or decyl benzoate.

13. The method of claim 9, wherein when the di- or polycarboxylic acid is partially esterified, fully esterified, or a combination thereof.

14. The method of claim 9, wherein the aromatic dicarboxylic acid is diisononyl phthalate or didecyl phthalate.

15. The method of claim 1, wherein the ester of the aromatic carboxylic acid comprises at least one ester group comprising at least one alcohol comprising a branched or an unbranched alkoxyalkyl, cycloalkyl or alkyl group comprising 1 to 25 carbon atoms, or a combination thereof.

16. The method of claim 1, wherein the ratio of the residence times in the series-connected loop reactors is from 0.01 to less than 1.

* * * * *